US007130747B1

(12) United States Patent
Von Dreele et al.

(10) Patent No.: US 7,130,747 B1
(45) Date of Patent: Oct. 31, 2006

(54) HIGH THROUGHPUT SCREENING OF LIGAND BINDING TO MACROMOLECULES USING HIGH RESOLUTION POWDER DIFFRACTION

(75) Inventors: Robert B. Von Dreele, Los Alamos, NM (US); Kevin D'Amico, Hinsdale, IL (US)

(73) Assignee: Los Alamos National Security, LLC, Los Alamos, NM (US)

( * ) Notice: Subject to any disclaimer, the term of this patent is extended or adjusted under 35 U.S.C. 154(b) by 496 days.

(21) Appl. No.: 09/871,527

(22) Filed: May 31, 2001

(51) Int. Cl.
*G06F 19/00* (2006.01)
(52) U.S. Cl. .............................. 702/27; 702/19; 435/4; 436/86
(58) Field of Classification Search .................. 702/27, 702/30
See application file for complete search history.

(56) References Cited

U.S. PATENT DOCUMENTS

| | | | |
|---|---|---|---|
| 5,434,796 A | 7/1995 | Weininger | |
| 5,571,902 A | 11/1996 | Ravikumar et al. | |
| 6,128,582 A | 10/2000 | Wilson et al. | |
| 6,177,280 B1 | 1/2001 | Yan et al. | |
| 6,229,010 B1 | 5/2001 | Crocker et al. | |
| 6,230,102 B1 | 5/2001 | Tidor et al. | |
| 6,297,021 B1 * | 10/2001 | Nienaber et al. | 435/7.1 |
| 6,667,299 B1 * | 12/2003 | Ahlem et al. | 514/178 |

OTHER PUBLICATIONS

Heiney. "What is X-ray diffraction (XRD)", 1996, on the world wide web at http://dept.physics.upenn.edu/~heiney/talks/hires/whatis.html#SECTION00014000000000000000, 4 pages.*
Yen-Ho Chu et al., "Affinity Capillary Electgrophoresis—Mass Spectrometry For Screening Combinatorial Libraries," J. Chem. Soc., vol. 118, pp. 7827-7835, 1996.
Robert Karlsson et al., "Kinetic Analysis of Monoclonal Antibody-Antigen Interactions with a New Biosensor Based Analytical System," Journal of Immunological Methods, vol. 145, pp. 229-240, 1991.
Shintaro Kumazawa et al., "Meed: A Program Package for Electron-Density-Distribution Calculation By the Maximum-Entropy Method," J. Appl. Cryst., vol. 26, pp. 453-457, 1993.
G. A. Slim, "A Note On the Heavy-Atom Method," Acta. Cryst., vol. 13, pp. 511-512, 1960.
Sidney Udenfriend et al., Scintillation Proximity Assay: A Sensitive and Continuous Isotopic Method for Monitoring Ligand/Receptor and Antigen/Antibody Interactions, Analytical Biochemistry, vol. 161, pp. 494-500, 1987.
R. B. Von Dreele, "Combined Rietveld and Stereochemical Restraint Refinement of a Protein Crystal Structure," J. Appl. Cryst., vol. 32, pp. 1084-1089, 1999.

Rex A. Palmer, "X-Ray Crystallographic Studies of Protein-Ligand Interactions," Chapter 1, pp. 1-98, 2001.
Romano T. Kroemer, "Molecular Modeling," Chapter 2, pp. 99-121, 2001.
G. N. Ramachandran, Fourier Methods in Crystallography, pp. 1-33, John Wiley & Sons, Inc., New York, 1970.
Bryan John Smith, "Protein Sequencing Protocols," pp. 17-24, Humana Press, Totowa, New Jersey, 1997.
Anthony w. Czarnik, "Accounts of Chemical Research," Acc. Chem. Res., vol. 29, No. 2, pp. 112-113, 1996.
Linda C. Hsieh-Wilson et al., "Lessons From the Immune System: From Catalysis to Materials Science," Acc. Chem. Res., vol. 29, No. 3, pp. 164-170, 1996.
Sheila Hobbs DeWitt et al., "Combinatorial Organic Synthesis Using Parke-Davis's Diversomer Method," Acc. Chem, Res, vol. 29, No. 3, pp. 114-122, 1996.
Robert W. Armstrong et al., "Multiple-Component Condensation Strategies for Combinatorial Library Synthesis," Acc. Chem. Res., vol. 29, No. 3, pp. 123-131, 1996.
Jonathan A. Ellman, "Design, Synthesis and Evaluation of Small-Molecule Libraries," Acc. Chem. Res., vol. 29, No. 3, pp. 132-143, 1996.
E. M. Gordon et al., "Strategy and Tactics in Combinatorial Organic Synthesis, Applications to Drug Discovery," Acc. Chem. Res., vol. 29, No. 3, pp. 144-154, 1996.
W. Clark Still, "Discovery of Sequence-Selective Peptide Binding by Synthetic Receptors Using Encoded Combinatorial Libraries," Acc. Chem. Res., vol. 29, No. 3, pp. 155-163, 1996.
Hideo Toraya, "Positions-Constrained and Unconstrained Powder-Pattern-Decomposition Methods," The Rietvels Method, Chapter 12, pp. 255-275, International Union of Crystallography, Oxford University Press, 1993.
R. B. Von Dreele, "Neutron Powder Diffraction," Modern Powder Diffraction, Reviews in Mineralogy, vol. 20, Chapter 11, pp. 331-369, 1989.

(Continued)

*Primary Examiner*—Marjorie A. Moran
*Assistant Examiner*—Carolyn L. Smith
(74) *Attorney, Agent, or Firm*—Bruce H. Cottrell

(57) ABSTRACT

A process is provided for the high throughput screening of binding of ligands to macromolecules using high resolution powder diffraction data including producing a first sample slurry of a selected polycrystalline macromolecule material and a solvent, producing a second sample slurry of a selected polycrystalline macromolecule material, one or more ligands and the solvent, obtaining a high resolution powder diffraction pattern on each of said first sample slurry and the second sample slurry, and, comparing the high resolution powder diffraction pattern of the first sample slurry and the high resolution powder diffraction pattern of the second sample slurry whereby a difference in the high resolution powder diffraction patterns of the first sample slurry and the second sample slurry provides a positive indication for the formation of a complex between the selected polycrystalline macromolecule material and at least one of the one or more ligands.

1 Claim, 2 Drawing Sheets

OTHER PUBLICATIONS

John w. Erickson et al., "Macromolecular X-Ray Crystallography and NMR As Tools for Structure-Based Drug Design," Annual Report in Medicinal Chemistry, vol. 27, pp. 271-289, 1992.

Martin R. Jefson, "Applications of NMR Spectroscopy to Protein Structure Determination," Annual Reports in Medicinal Chemistry, vol. 23, pp. 275-283, 1988.

U. Jonsson et al., "Real-Time Biospecific Interaction Analysis Using Surface Plasmon Resonance and a Sensor Chip Technology," Biotechniques, vol. 11, No. 5, pp. 620-627, 1991.

R. B. Von Dreele, "Protein-Drug Interaction," Modern Drug Discovery, vol. 4, No. 5, pp. 83-84, May 2001.

Melinda Balbirnie et al., "An Amyloid-Forming Peptide From the Yeast Prion Sup35 Reveals a Dehydrate β-Sheet Structure for Amyloid," Proc. Nat. Sci., vol. 98, No. 5, pp. 2375-2380, Feb. 27, 2001.

J. D. Bernal et al., "X-Ray and Crystallographic Studies of Plant Virus Preparations. III," Journal of General Physiology, vol. 25, pp. 147-165, 1941.

W. F. van Gunsteren et al., "Biomolecular Simulation: The Gromos96 Manual and User Guide," Biomos b.v., Zurich, Groningen, pp. 1-123, 1996.

Jan Drenth, "Principles of Protein X-Ray Crystallography," Chapter 2, pp. 22-47, Springer Advanced Texts in Chemistry, 1999.

Allen C. Larson et al., "General Structrure Analysis System (GSAS)," Los Alamos National Laboratory Report, LAUR 86-748, pp. 1-224, 2001.

* cited by examiner

HIGH THROUGHPUT SCREENING OF LIGAND BINDING TO MACROMOLECULES USING HIGH RESOLUTION POWDER DIFFRACTION

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates to a process for detecting or screening possible interactions between a selected target macromolecule or protein and a suite of possible small molecule ligands.

BACKGROUND OF THE INVENTION

With the decoding of the human and other genomes, the paradigm of drug discovery is expected to change to one that is focused on molecular design for interaction with specific proteins. This new emphasis on proteomics will require experimental verification of the details of protein/ligand interactions under a wide variety of conditions. Current techniques either require formation of single crystals of sufficient quality of the protein/ligand complex for x-ray diffraction work or else interpretation of NMR spectra. This work is difficult as indicated by a cursory examination of the Protein Data Base that shows only about 10% of the entries involve protein/ligand complexes.

Present screening methods for protein-ligand interaction often involve either: (1) the selective displacement of a dye molecule by the ligand thus provoking a change in the optical spectrum; or (2) performance of detailed single crystal structure determinations on every potential protein-ligand complex to determine the presence or absence of the ligand molecule in the protein structure. The former method requires selection and development of a suitable dye that interacts with the protein in the same way a presumed ligand might interact. Dyes that interact in different ways will not show a clear and definitive test for a ligand binding in the active site of the protein. In the latter method, the fundamental requirements for the single crystal test involve the ability to produce quantities of suitable single crystals for the ligand binding tests and that the single crystal survives the formation of the protein-ligand complex. As these two requirements are frequently not fulfilled for a chosen protein target, a quicker, more robust method has been desirable for detecting or screening possible interactions between a selected target macromolecule or protein and a suite of possible small molecule ligands.

It is an object of the present invention to provide a process for process that can be used to detect or screen possible interactions between a selected target macromolecule or protein and a suite of possible small molecule ligands.

SUMMARY OF THE INVENTION

In accordance with the purposes of the present invention, as embodied and broadly described herein, the present invention provides a process for the high throughput screening of binding of ligands to macromolecules using high resolution powder diffraction data including producing a first sample slurry of a selected polycrystalline macromolecule material and a solvent, producing a second sample slurry of a selected polycrystalline macromolecule material, one or more ligands and said solvent, obtaining a high resolution powder diffraction pattern on each of said first sample slurry and said second sample slurry, and, comparing the high resolution powder diffraction pattern of said first sample slurry and the high resolution powder diffraction pattern of said second sample slurry whereby a difference in the high resolution powder diffraction patterns of said first sample slurry and said second sample slurry provides a positive indication for the formation of a complex between said selected polycrystalline macromolecule material and at least one of said one or more ligands.

The present invention further provides a process of high throughput screening of binding of ligands to macromolecules using high resolution powder diffraction data including producing a sample slurry mixture including a selected polycrystalline macromolecule material, a solvent, and a mixture of N ligands, obtaining a high resolution powder diffraction pattern of said sample slurry mixture, comparing the high resolution powder diffraction pattern of said sample slurry mixture with a reference of a high resolution powder diffraction pattern of said selected polycrystalline macromolecule material in the absence of any ligands whereby a difference in the high resolution powder diffraction patterns of said sample slurry mixture and said selected polycrystalline macromolecule material in the absence of any ligands provides a positive indication for the formation of a complex between said selected polycrystalline macromolecule material and at least one of said mixture of N ligands, dividing said mixture of N ligands into at least two sample slurry groups by forming at least a first sample slurry including said selected polycrystalline macromolecule material, said solvent, and a mixture of selected ligands from among the N ligands, and forming at least a second sample slurry including said selected polycrystalline macromolecule material, said solvent, and a mixture of selected ligands not in said first sample slurry, wherein all of said N ligands are present in at least one of said sample slurry groups, repeating steps of obtaining high resolution powder diffraction patterns, and steps of comparing said high resolution powder diffraction patterns whereby a difference in high resolution powder diffraction patterns between a said sample slurry and said selected polycrystalline macromolecule material in the absence of any ligands provides a positive indication for the formation of a complex between said selected polycrystalline macromolecule material and at least one ligand within said sample slurry, and, repeating steps of dividing said mixture of selected ligands for any sample slurry exhibiting a positive indication for the formation of a complex between said selected polycrystalline macromolecule material and at least one ligand within said slurry sample into at least two additional sample slurry groups, steps of obtaining high resolution powder diffraction patterns, and steps of comparing said high resolution powder diffraction patterns until all ligands within said mixture of N ligands that show binding have been identified.

DETAILED DESCRIPTION

The present invention concerns a process that can be used to detect or screen possible interactions between a selected target macromolecule or protein and a suite of possible small molecule ligands. The indication for this interaction or binding is a change in a high resolution powder diffraction pattern of the target protein or macromolecule as compared to the unbound form of the target protein or macromolecule which is the result of a modification of its crystal structure upon formation of a protein-ligand complex. For example, the comparison between patterns can be of the positions of diffraction peaks in the two patterns. In one embodiment, the process is a search approach in which tests of the binding between the target protein or macromolecule and a sequence of ligand mixtures is then used as a rapid means of identifying those ligands that bind to the target protein or macromolecule. One approach can be a binary search approach.

Figure 1:
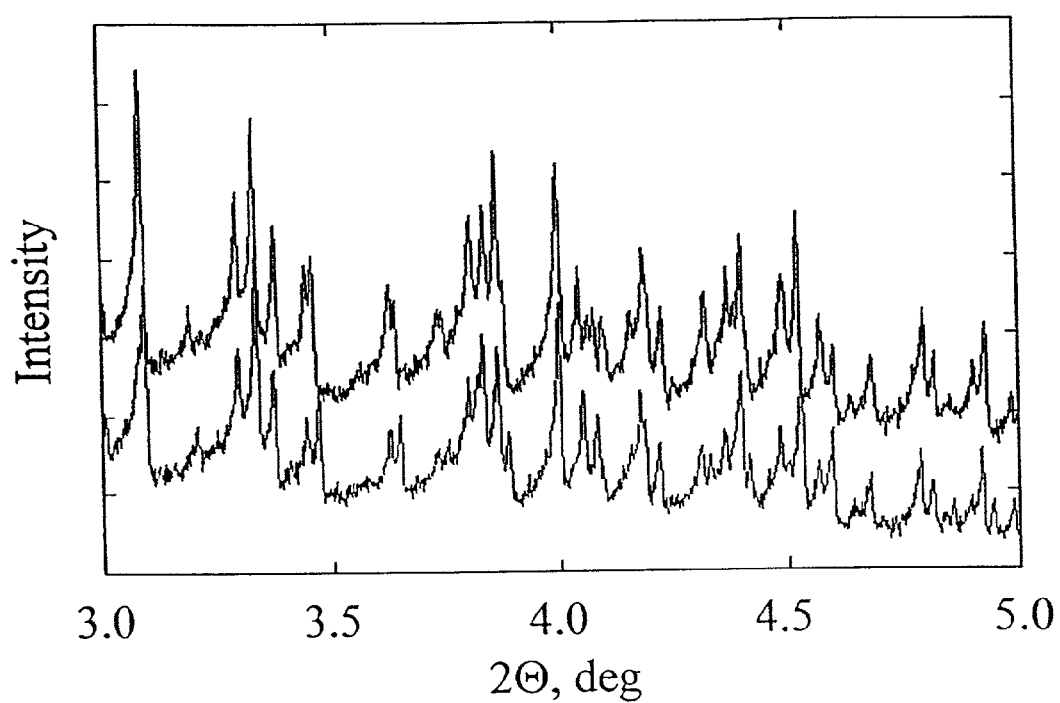
FIG. 1 shows a comparison plot in accordance with the present invention of a small segment of high resolution x-ray powder diffraction patterns of lysozyme (bottom pattern) in comparison to a lysozyme/N-acetylglucosamine mixture (top pattern) precipated from pH6.0 0.5 M NaCl buffer taken with $\gamma=0.70$ Å. The latter pattern has been offset for clarity.

The screening method of the present invention can be as follows. Two samples of polycrystalline material are produced as slurries. One of the samples includes the target protein or macromolecule and a suitable solvent. The other of the samples includes the target protein or macromolecule, one or more selected ligands and the same solvent as in the first sample. High resolution powder diffraction patterns are obtained for each sample. The patterns from the first and second samples are then compared to see if there is any discernable difference between the two sets of diffraction patterns. When there is a discernable difference between the two sets of diffraction patterns, that is a positive indication for the formation of a complex between the target protein or macromolecule and one or more of the selected ligands. Generally, a simple visual inspection can be used to determine if there is a difference as can be seen in FIG. 1. In another manner, the pattern of the first sample can be inspected or analyzed to determine the positions of the diffraction peaks from the unbound form of the target protein or macromolecule, while the pattern of the second sample can be inspected or analyzed to determine the positions of the diffraction peaks from the target protein or macromolecule in the presence of the one or more selected ligands. Differences in such diffraction peaks can then be used to determine if there is a difference indicating binding of a ligand. This process is readily automated via computerized data processing routines A more detailed screening process for a larger suite of ligands and a single target protein or macromolecule could be as follows. Such a screening process can be a binary search approach as follows or may be other than a binary approach, i.e., division can be into as many sample slurries as desired. In a binary embodiment, a mixture of "N" ligands is produced in a single solution. A preferred embodiment is for the case where $N=2^n$, i.e., where N is 2, 4, 8, 16, 32 and the like. A target protein or macromolecule is then exposed to the single solution of ligands thereby producing a slurry of polycrystalline material. A screening procedure is conducted wherein high resolution powder diffraction patterns are obtained for the sample. The diffraction pattern is then compared to a reference diffraction pattern from a sample of the unbound form of the target protein or macromolecule. When there is a discernable difference between the two diffraction patterns, that is a positive indication for the formation of a complex between the target protein or macromolecule and one or more of the selected ligands. In one manner, the pattern of the sample is inspected or analyzed to determine the positions of the diffraction peaks from the target protein or macromolecule in the presence of the one or more selected ligands and compared to a reference set of diffraction peaks from a sample of the unbound form of the target protein or macromolecule.

Where there is a positive indication of an interaction, then there is one or more ligands among the "N" ligands in the mixture that bind to the target protein or macromolecule. In a binary approach, two mixtures of ligands are then formed so that one mixture contains "N/2" of the ligands and the other mixture contains the remaining "N/2" of the ligands. Following the previous procedure, the target protein or macromolecule is exposed to each of the two ligand mixtures to determine which mixture contains one or more ligands that produced the positive indication of binding. This divisional process is repeated until all ligands in the original mixture that show binding to the target protein or macromolecule are identified.

In such a binary search process, the number of tests required to determine a single ligand with a positive indication of binding with the target protein or macromolecule from amongst a suite of $N=2^n$ ligands is $2(n)+1$. For example, if N=64, then the number of tests required would be 13.

Automation of the steps in this invention will be readily achievable by one skilled in the art of automated processes.

Powder diffraction from polycrystalline slurries is far more robust because the experimental conditions (solvent pH, ion concentration and the like) for obtaining polycrystalline material is much broader and can be more tightly controlled than for growing large single crystals. In addition, crystal fracture during protein-ligand formation is essentially irrelevant in a powder diffraction experiment as the material is polycrystalline anyway.

This invention should be useful for screening potential pharmaceutical materials for binding to a protein that was previously identified as a crucial component in a target organism (bacterial, viral, etc.). Following this identification of potential activity, further studies can be pursued to determine the usefulness of this material as a drug. In addition, this invention can be used to identify the mode or modes of action for a particular protein by exposing it to a suite of ligands that encompass its possible modes of action. Then, the mode of interaction can be determined by, e.g., examining the results from a single crystal diffraction study of a crystal grown of the protein-ligand complex.

Recent studies have shown that powder diffraction may be a useful tool for examining protein structures. Powder diffraction patterns can display considerable sensitivity to subtle structural changes via shifts in the diffraction peak positions and changes in intensity. Such studies showed that protein lattice parameter determinations from powder data are perhaps two orders of magnitude more precise than those obtained from typical single crystal experiments and that combined Rietveld refinements (see Rietveld, J. Appl. Crys., vol. 2, pp. 65–71 (1969) and stereochemical restraint refinements can give protein structures of moderate (~3 Å) resolution.

For the study of protein/ligand complexes, powder diffraction offers a distinct advantage over single crystal work in its complete immunity to crystal fracture or even a phase change that may accompany complex formation. Moreover, rapid formation of a polycrystalline precipitate allows possible exploration of initial complex formation under a wide variety of conditions not accessible in slow soaking or single crystal growth experiments. The use of high resolution X-ray powder diffraction for protein/ligand structure determination in a study of the binding of N-acetyglucosamine to chicken egg lysozyme has now been demonstrated.

Previous high-resolution X-ray powder diffraction studies with metmyoglobin and $T_3R_3$ Zn insulin complexes used samples obtained by grinding previously crystallized protein in its mother liquor and yielded material with extremely sharp diffraction peaks and little or no sample broadening.

Figure 2:
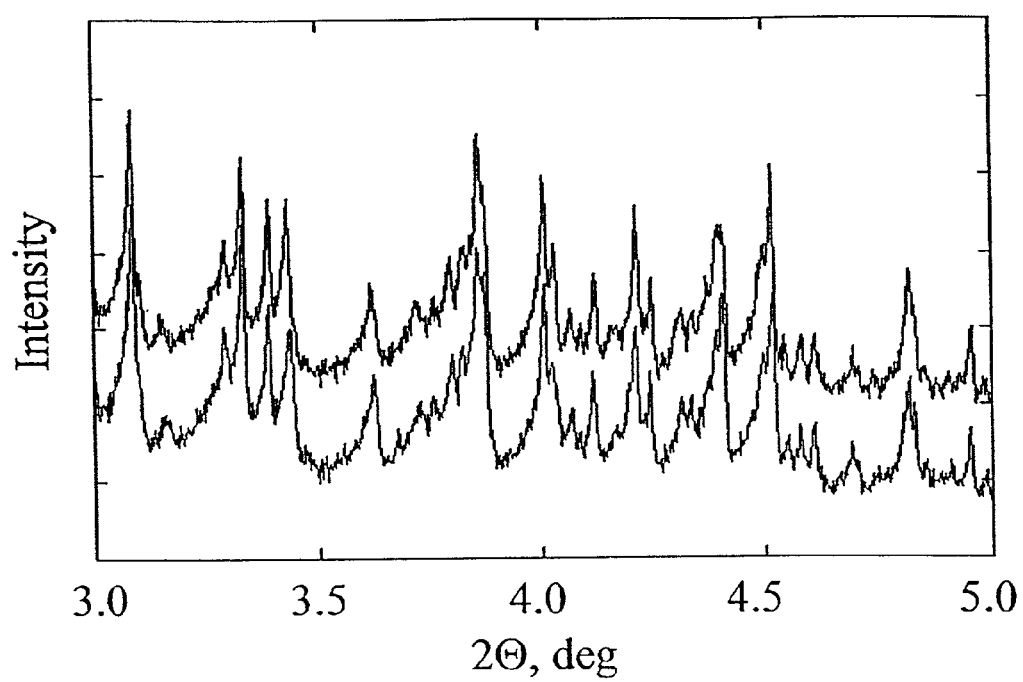
FIG. 2 shows a comparison plot in accordance with the present invention of a small segment of high resolution x-ray powder diffraction patterns of lysozyme (bottom pattern) in comparison to a lysozyme/N-acetylglucosamine (top pattern) mixture precipated from pH 5.0 0.5 M NaCl buffer taken with γ=0.70 Å. The latter pattern has been offset for clarity.

In this embodiment of the present invention, the lattice parameters of lysozyme and α-NAG/lysozyme complex (Table 1) have been determined with unprecedented precision via powder diffraction. The precision obtained here approaches one part in 80,000 and is the result of Rietveld refinement fitting of the entire powder diffraction profile and the extreme sharpness of the peaks. Similar precision was obtained in earlier powder diffraction studies of metmyoglobin and Zn insulin complexes (see Von Dreele, J. Appl. Cryst., vol. 32, pp. 1084–1089 (1999) and Von Dreele et al., Acta Cryst., vol. D56, pp. 1549–1553 (2000)). Consequently small changes in these values with pH and complex formation are readily apparent and can even be discerned from a simple visual comparison (FIGS. 1 & 2).

Formation of the α-NAG/lysozyme complex from pH 6.0 0.5 M NaCl was marked by easily visible changes in the powder diffraction patterns (FIG. 1) and significant changes in the lattice parameters. For the complex, a is smaller by 0.21% and c larger by 0.49% compared to those of the apo-protein precipitated from the same buffer. This change upon complex formation is consistent with the lower precision single crystal values obtained by Perkins et al., Biochem. J., vol. 173, pp. 607–616 (1978) and, interestingly, those obtained by Cheetham et al. J. Mol. Biol., vol. 224, pp. 613–628 (1992) for the $NAG_3$/lysozyme complex. The precipitate from a NAG/lysozyme mixture in pH 5.0 0.5 M NaCl showed no visible change in the powder pattern (FIG. 2) from that of pure lysozyme prepared from the same solvent and the lattice parameters are also essentially unchanged (a smaller by 0.06% and c larger by 0.15%).

Clearly, as observed earlier for metmyoglobin and $T_3R_3$ Zn, polycrystalline lysozyme and NAG/lysozyme powders, prepared in this case by rapid precipitation, consist of essentially defect free crystallites that are a few microns across. These dimensions suggest that the crystallites are only a few hundred protein unit cells in extent which, when coupled with the relatively weak binding between adjacent molecules, is insufficient to retain point and line defects at ambient temperature. Consequently, powder diffraction patterns of these materials give diffraction peaks that are as sharp as can be obtained from a given diffraction instrument; this may be a common feature of ambient temperature protein powder diffraction patterns. In essence, proteins are "perfect" powders for diffraction thus ensuring application of this invention to a wide variety of proteins. Here, the extreme sharpness of these patterns arose from the uniform and easily controlled precipitation conditions and allowed easy discernment of the small structural changes associated with protein/ligand complex formation and ready discrimination from cases where no complex is formed. Moreover, the quality of the powder diffraction pattern was sufficient to determine the detailed structural features of the protein/ligand complex. Thus, high-resolution powder diffraction can facilitate the screening for protein/ligand interactions and may facilitate the determination of their resulting structures under a wide variety of conditions.

The present invention is more particularly described in the following example which is intended as illustrative only, since numerous modifications and variations will be apparent to those skilled in the art.

Example 1

Chicken egg lysozyme (EC 3.2.1.17, FisherBiotech, 3× crystallized, lot Nos. 995417-12 and 996924-12) and N-acetylglucosamine (NAG, ICN Biomedicals, Inc. lot No. R9745), pH 6.0 0.05 M $Na_2HPO_4/KH_2PO_4$ buffer (Fisher Sci.), pH 5.0 0.05 M KHphthalate/NaOH buffer (Hydrion™, Aldrich Chem.) and NaCl ("Certified for Biological Use", Fisher Sci.) were used as received. In a typical sample preparation, a polycrystalline slurry was made by combining ~20 mg lysozyme (1.4 μmol), about 10 mg of NAG (45 μmol) and 200 μl of 0.5 M NaCl pH 6.0 buffer with an agate mortar and pestle. Polycrystalline precipitate formed within a few seconds. The slurry was loaded into a 1.5 mm diameter glass capillary, and centrifuged to pack the slurry. Excess mother liquor was removed and the capillary flame sealed to prevent subsequent solvent evaporation. In a similar way, a polycrystalline sample of unbound lysozyme in pH 6.0 0.5 M NaCl buffer was prepared. Similar samples with pH 5.0 0.5 M NaCl buffer were also prepared. Samples were about 8 mm long. As each sample was prepared, X-ray powder diffraction data were immediately collected at room temperature (23° C.) on beam line X3b1 at the National Synchrotron Light Source, Brookhaven National Laboratory, equipped with a double Si(111) monochromator and a Ge(111) analyser; the sample was spun during data collection to ensure good powder averaging. Details of the data collections are given in Table 1.

TABLE 1

Crystallographic data for N-acetyl-D-glucosamine/lysozyme complexes*

| Material | lysozyme | NAG/ lysozyme | lysozyme | NAG/ lysozyme |
|---|---|---|---|---|
| Crystal data: | | | | |
| Space group | $P4_32_12$ | $P4_32_12$ | $P4_32_12$ | $P4_32_12$ |
| a (Å) | 79.1317(11) | 78.9631(10) | 78.5689(15) | 78.5240(14) |
| c (Å) | 38.0297(10) | 38.2151(10) | 38.5134(15) | 38.5731(14) |
| V (Å$^3$) | 238135(8) | 238277(9) | 237746(12) | 237842(12) |
| Powder data collection: | | | | |
| Buffer pH | 6.00 | 6.00 | 5.00 | 5.00 |
| Measured pH | 5.2 | 5.1 | 4.8 | 4.8 |
| λ (Å) | 0.699970(1) | 0.699842(1) | 0.700030(1) | 0.700030(1) |
| 2Θ range (°) | 1.0–13.580 | 1.0–13.498 | 1.0–13.994 | 1.0–13.698 |
| ΔΘ (°) | 0.002 | 0.002 | 0.002 | 0.002 |
| Steps | 6291 | 6250 | 6497 | 6350 |
| Step time (s) | 4.0–11.25 | 4.0–11.13 | 4.0–12.04 | 4.0–11.51 |

*NAG = N-acetylglucosamine. Values in parentheses are estimated standard deviations in the values shown. pH measurements were taken with a LAZAR Research Laboratories PHR-146 Micro Combination electrode calibrated with pH 4.00 and pH 7.00 standard buffers (Fisher Sci.). Wavelength calibrations were obtained from the fitted positions of six reflections from a NIST SRM1976 alumina plate. Data collection step count times were determined by the following algorithm: for 2Θ < 5° t = 4s; for 2Θ > 5°
t = 6.469 − 0.9877(2Θ) + 0.0988(2Θ)$^2$s.

Visual comparison of the diffraction patterns obtained from lysozyme and NAG/lysozyme polycrystalline slurries formed in the pH 6.0 0.5 M NaCl buffer (FIG. 1) clearly show that a structural modification has occurred associated with the formation of a NAG/lysozyme complex. The patterns show differences in peak positions, which arise from lattice parameter changes, and differences in intensity associated with the crystal structure modification. There were no changes evident in a comparison of the powder patterns of lysozyme and NAG/lysozyme slurries prepared with pH 5.0 0.5 M NaCl buffer (FIG. 2).

Although the present invention has been described with reference to specific details, it is not intended that such details should be regarded as limitations upon the scope of the invention, except as and to the extent that they are included in the accompanying claims.

What is claimed is:

1. A process for high throughput screening of binding of ligands to macromolecules using high resolution powder diffraction data comprising:

producing a first sample slurry of a selected polycrystalline macromolecule material and a solvent, wherein said selected polycrystalline macromolecule material comprises a protein;

producing a second sample slurry of said selected polycrystalline macromolecule material, one or more ligands and said solvent;

obtaining a high resolution powder diffraction pattern on each of said first sample slurry and said second sample slurry; and, comparing the high resolution powder diffraction pattern of said first sample slurry and the high resolution powder diffraction pattern of said second sample slurry whereby a change between the high resolution powder diffraction patterns of said first sample slurry and said second sample slurry indicates formation of a complex between said selected polycrystalline macromolecule material and at least one of said one or more ligands.

* * * * *